United States Patent [19]
Boyd et al.

[11] Patent Number: 5,185,266
[45] Date of Patent: Feb. 9, 1993

[54] CLEAVAGE METHOD FOR ACYL THIOHYDANTOINS AND USE OF THE METHOD IN C-TERMINAL PEPTIDE SEQUENCING

[75] Inventors: Victoria L. Boyd; Gerald Zon, both of San Carlos, Calif.

[73] Assignee: Applied Biosystems, Inc., Foster City, Calif.

[21] Appl. No.: 775,771

[22] Filed: Oct. 15, 1991

[51] Int. Cl.$^5$ ............................................. G01N 33/68
[52] U.S. Cl. ..................................... 436/89; 436/161; 530/345; 530/402; 530/412
[58] Field of Search ................... 436/89, 90, 161, 172; 530/343, 344, 345, 402, 407–410, 412

[56] References Cited

U.S. PATENT DOCUMENTS

| | | | |
|---|---|---|---|
| 4,837,165 | 6/1989 | Hawke | 436/89 |
| 5,041,388 | 8/1991 | Boyd et al. | 436/89 |
| 5,049,507 | 9/1991 | Hawke et al. | 436/89 |
| 5,059,540 | 10/1991 | Bailey | 436/89 |

OTHER PUBLICATIONS

Laursen, R. A., et al., "Solid-Phase Methods in Protein Sequence Analysis" in Methods of Biochemical Analysis 26:201–284 (1980).
Miller, C. G., et al., in "Techniques in Protein Chemistry", (Hugh, T. E., ed.), Academic Press, pp. 67–78 (1989).
Miller, C. G., et al., Abstract T188 from the Third Symposium of the Protein Society, Seattle, Wash. (Jul. 29–Aug. 2, 1989).
Schlack, P., et al., Hoppes Seylers Z. Physical Chemistry, 154:126–171 (1926).
Edman, P., Acta Chem. Scand., 4:283–294, 277–282 (1950).
Edman, P., Acta Chem. Scand., 10:761–768 (1956).
Boyd, V. L., et al., Tetrahedron Letters 31:3849–3852 (1990).
Hendrickson et al., Organic Chemistry, 3rd Ed., pp. 697–738, McGraw-Hill, New York, New York (1970).
Inglis, A. S., Analytical Biochemistry, 195:183–196 (1991).

Primary Examiner—James C. Housel
Assistant Examiner—David Redding
Attorney, Agent, or Firm—Joseph A. Smith; Peter J. Dehlinger

[57] ABSTRACT

Disclosed is a method for enhancing the cleavage of an acyl thiohydantoin bond, for example, for use in C-terminal peptide sequencing. An acyl thiohydantoin is alkylated to form an adduct on the thiohydantoin, and the adduct-containing thiohydantoin is cleaved at its acyl bond by reaction with a cleaving agent under substantially anhydrous, acidic conditions. In C-terminal amino acid sequencing, the cleaved product is analyzed to identify the C-terminal amino acid.

11 Claims, 13 Drawing Sheets

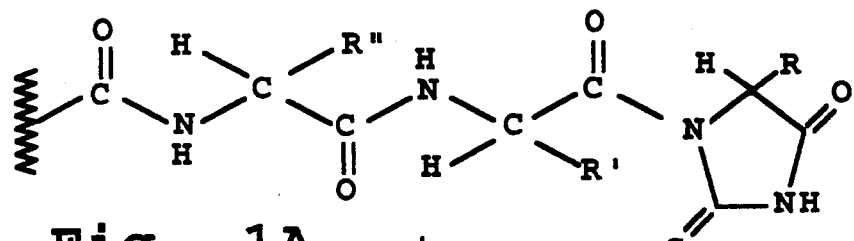
Fig. 1A
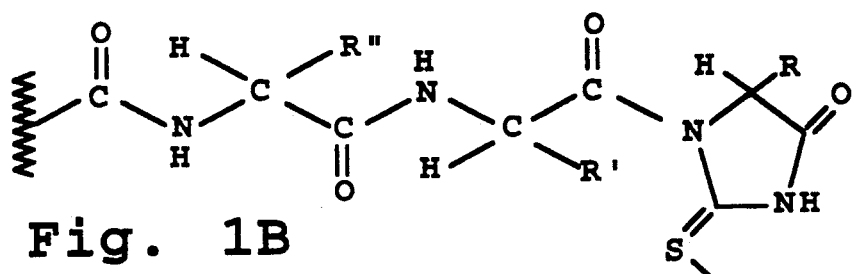
Fig. 1B
↓ Substantially anhydrous TFA
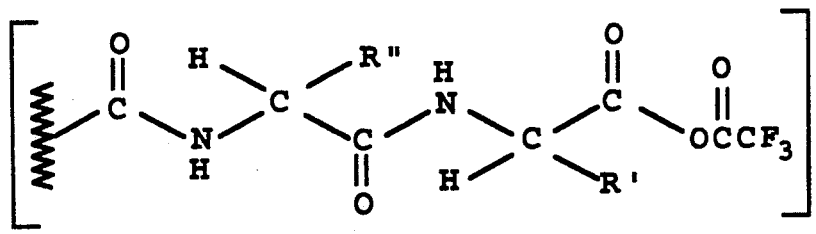
Fig. 1C    +    Modified, cleaved thiohydantoin derivative
↓ $H_2O$
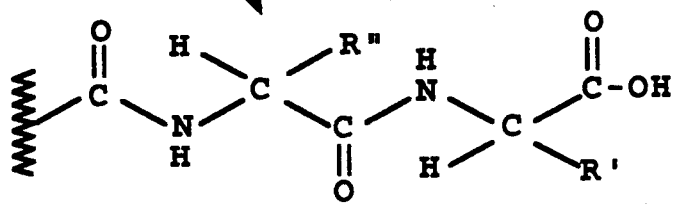
Fig. 1D

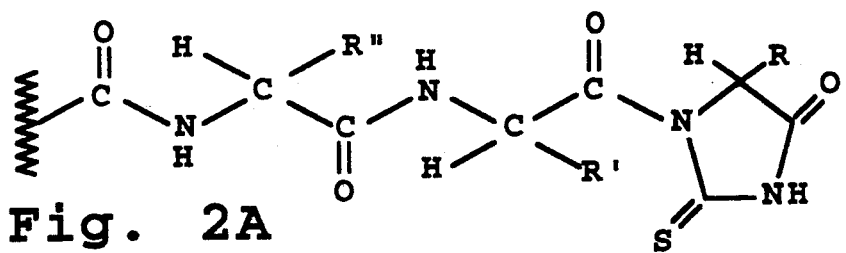
Fig. 2A
↓ XR₂/Base
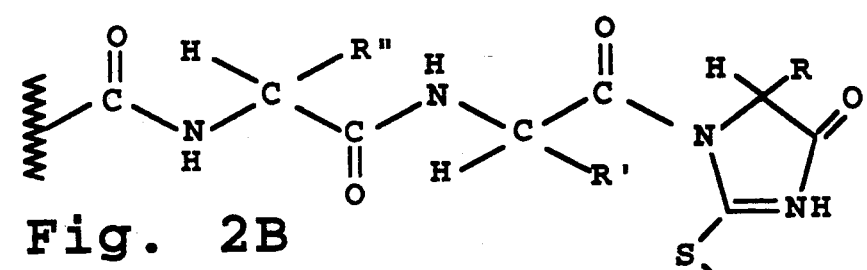
Fig. 2B
↓ Substantially anhydrous TMS-ITC
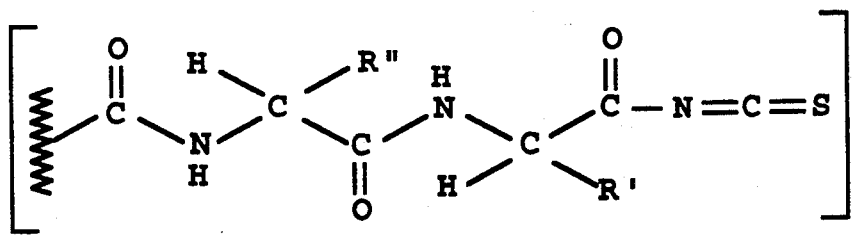
Fig. 2C        +
Cleaved, modified thiohydantoin derivative
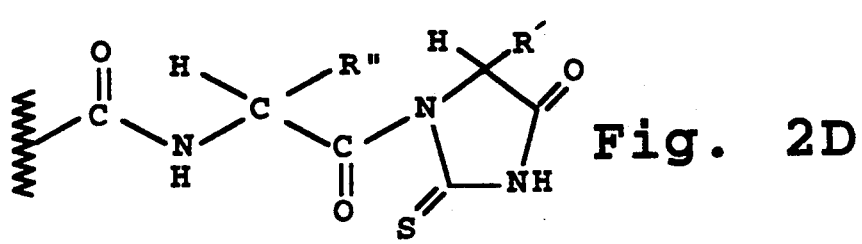
Fig. 2D

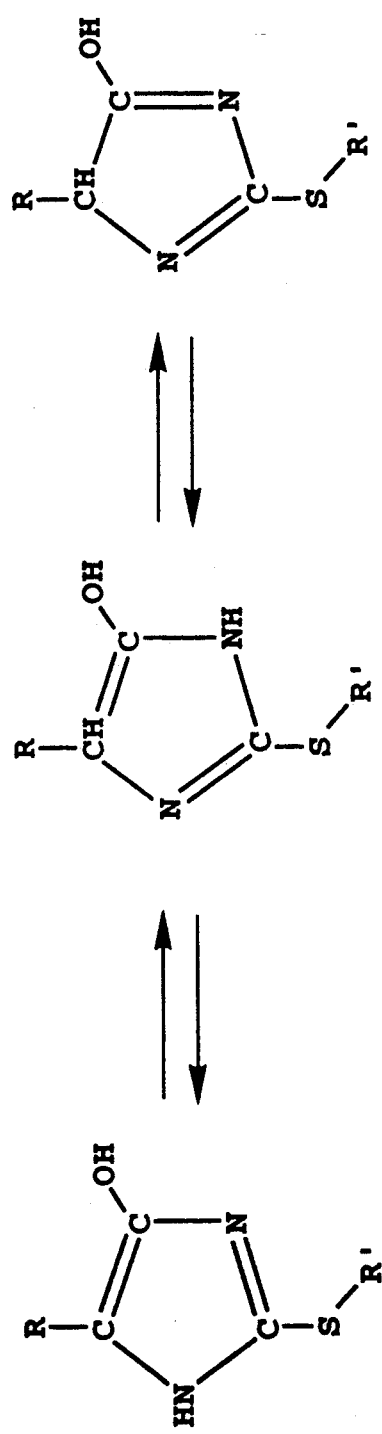

CLEAVAGE METHOD FOR ACYL THIOHYDANTOINS AND USE OF THE METHOD IN C-TERMINAL PEPTIDE SEQUENCING

FIELD OF THE INVENTION

The present invention relates to improved methods for cleaving an acyl thiohydantoin bond, and use of the method in C-terminal amino acid sequencing.

REFERENCES

The following references are cited in this application.
Edman, P., Acta Chem. Scand., 4:283–294 (1950);
Edman, P., Acta Chem. Scand., 10:761–768 (1956);
Boyd et al., U.S. Pat. No. 5,051,368;
Boyd et al., Tetrahedron Letters, 31:3849–3852 (1990);
Hawke, D. H., et al., U.S. Pat. No. 5,049,507;
Hawke, D. H., et al., U.S. Pat. No. 5,041,388;
Hendrickson et al., Organic Chemistry, 3rd Ed., pp. 697–738, McGraw-Hill, New York, N.Y. (1970);
Meuth, J. L., et al., Biochemistry, 21:3750–3757(1982);
Bailey et al., Biochemistry, 29:3145–3156 (1990);
Miller, C. G., et al., Abstract T188 from the Third Symposium of the Protein Society, Seattle, Wash. (July 29–August 2, 1989);
Miller, C. G., et al., in "Techniques in Protein Chemistry", (Hugh, T. E., ed.), Academic Press, pp. 67–78 (1989);
Parham, M. E., et al., Biochem. Biophys. Res.Commun., 80:7 (1978);
Schlack et al., Hoppes Seylers Z. Physical Chemistry, 154:126–171 (1926);
Stark, G. R., Methods in Enzymology, 29:369–384 (1969);
Stark, G. R., Biochemistry, 7:1796–1807 (1968);
Inglis, A., Analytical Biochemistry, 195:183–196 (1991);
Laursen et al., "Solid-Phase Methods in Protein Sequence Analysis" in Methods of Biochemical Analysis, 26:201–284, Glick - Editor, John Wiley & Sons (1980);

BACKGROUND OF THE INVENTION

The determination of the amino acid sequence of a peptide is essential to understanding its structure, as well as to modifying the peptide to achieve desired properties in an analog or mimetic. The most widely used method of peptide sequencing involves reacting at the N-terminus with phenyl isothiocyanate (PITC), a process known as Edman degradation (Edman). The reaction of PITC with the terminal amino group adds a phenylthiourea group, which cyclizes and cleaves, forming a free anilinothiozolanone (ATZ) of the N-terminal amino acid, and a shortened peptide. The ATZ-derivative of the N-terminal amino acid is separated, converted to the corresponding phenylthiohydantoin (PTH), and identified by HPLC.

N-terminal sequencing is carried out by successively converting the next-in N-terminal amino acid to the free amino acid PTH, and identifying each successively released amino acid. The method is generally reliable for sequences up to about 20–40 amino acid residues and is readily performed with automated instrumentation. Of course, for longer polypeptides, C-terminal sequence information is not available by N-terminal sequencing.

Several methods have been proposed for C-terminal peptide sequencing, based in methods which are primarily enzymatic, physical, or chemical. The enzymatic strategy involves analyzing the amino acids released from treatment of the peptide with carboxypeptidases. It is impeded by difficulties in controlling the extent, the rate and the specificity of enzymatic cleavages.

The most common physical tools used for C-terminal sequencing are fast atom bombardment mass spectrometry (FAB/MS), and nuclear magnetic resonance (NMR) spectroscopy. FAB/MS analysis is applicable to 1–10 nmole amounts of peptide, but requires expensive mass spectrometry equipment. Sequence determination by NMR utilizes large amounts of peptide, typically in the μmolar range, and also involves expensive equipment.

In view of the limitations of enzymatic and physical approaches to C-terminal sequencing, considerable effort has been invested in developing chemical methods for determining C-terminal amino acids residues, and for C-terminal sequencing. An inherent difficulty in C-terminal sequencing is the relative chemical inertness of the carboxyl/carboxylate group, in contrast to the reactivity of the amino group.

Several chemical methods have been proposed for C-terminal sequencing (Inglis). One of these involves generating a carboxyamido derivative at the C-terminal end of the peptide, followed by derivitization with bis-(I,I-trifluoro-acetoxy)iodobenzene, and hydrolysis to form a shortened carboxyamidopeptide and the aldehyde derivative of the C-terminal amino acid (Parham). A second and related approach involves reacting the carboxyl terminus with pivaloylhydroxamide to effect a Lossen rearrangement. One limitation of this method is that it does not progress beyond aspartic or glutamic acid residues (Miller, 1977).

The most widely studied of the C-terminal sequencing chemistries is the thiohydantoin (TH) reaction. In one general procedure for carrying out the thiohydantoin method, the carboxyl group is activated with an anhydride, in the presence of an isothiocyanate (ITC) salt or acid, to form a C-terminal peptidylthiohydantoin via a C-terminal ITC intermediate (Stark). The thiohydantoin is a ring formation which includes the nitrogen, chiral carbon and carbonyl of the terminal amino acid. It is attached to the remainder of the peptide through the bond which was the amide bond between the C-terminal and penultimate amino acids. The C-terminal thiohydantoin can be cleaved at that amide bond, producing a shortened peptide and the thiohydantoin derivative of the C-terminal amino acid. This derivative can be separated and identified, e.g., by high performance liquid chromatography (HPLC).

However, the chemical reactions used in thiohydantoin-based methods present two significant disadvantages when applied in amino acid sequencing. The initial formation of the C-terminal amino acid thiohydantoin typically requires long reaction times with highly reactive agents, such as anhydrides. (Meuth, Shively et al.). Such conditions often lead to chemical alterations of the peptide. The second drawback encountered with TH reactions is the difficulty in efficiently cleaving the C-terminal amino acid thiohydantoin from the peptide. Since the thiohydantoin group is not a good leaving group, strong reagents (e.g., a strong acid, base or nucleophile) and fairly vigorous conditions are required to achieve efficient cleavage, again compromising the integrity of the remaining peptide.

Recent efforts for improving thiohydantoin chemistry have focused on improving the efficiency of the C-terminal amino acid thiohydantoin formation. For example, Boyd et al., U.S. Ser. No. 07/546,303 discloses improved methods of C-terminal amino acid thiohydantoin formation which can be carried out under milder conditions. Hawke et al., U.S. Ser. No. 07/454,666 and U.S. Ser. No. 07/457,088, also discloses improved methods for thiohydantoin formation. The disclosures of each of these references is incorporated herein by reference in their entirety.

SUMMARY OF THE INVENTION

It is one general object of the invention to provide an improved method of cleaving an acyl-thiohydantoin bond, such as a peptidyl-thiohydantoin bond.

A related object of the invention is to provide an improved method of C-terminal amino acid sequencing.

The invention includes, in one aspect, a method for cleaving the acyl-thiohydantoin bond in an acyl thiohydantoin. This method includes (a) contacting the acyl thiohydantoin with an alkylating agent under conditions effective to form an adduct on the thiohydantoin by alkylation; and (b) reacting the adduct-containing acyl-thiohydantoin from (a) above with a cleaving agent under substantially anhydrous, acidic conditions to cause cleavage of the acylthiohydantoin bond, with release of an adduct-containing thiohydantoin.

When used in C-terminal amino acid sequencing, the acyl thiohydantoin is a peptidyl thiohydantoin formed at the C-terminal amino acid of said peptide, with the acyl thiohydantoin containing the side chain of the C-terminal amino acid. The alkylating which is contacted with the thiohydantoin preferably includes a label, such as a fluorescent or other optically absorbing moiety by which the released thiohydantoin can be detected. The released adduct-containing thiohydantoin can be distinguished (identified) by its particular amino acid side chain, e.g., using HPLC.

Also in a preferred amino acid sequencing method, the cleaving agent is an isothiocyanate, and the cleaving is effective to produce an acyl thiohydantoin with the penultimate C-terminal amino acid. A preferred cleaving agent is trimethylsilyl isothiocyanate.

In a more particular embodiment, for use in C-terminal amino acid sequencing of a polypeptide, the method includes the steps of first converting the C-terminal amino acid of the polypeptide to an acyl-thiohydantoin which is joined to the penultimate C-terminal amino acid through an acyl-thiohydantoin bond. The thiohydantoin is then contacted with an alkylating agent under conditions effective to form an adduct on the thiohydantoin by alkylation. The adduct-containing acyl-thiohydantoin from (b) is reacted with a cleaving agent under substantially anhydrous, acidic conditions to cause cleavage of the acyl-thiohydantoin bond, with release of an adduct-containing thiohydantoin from the remaining, shortened polypeptide. The C-terminal of the shortened polypeptide is converted to an acyl-thiohydantoin, and the above steps are repeated.

Each successive adduct-containing thiohydantoin which is released is isolated and identified, e.g., by HPLC, according to its characteristic amino acid side. The method has been used for sequencing of up to 10 C-terminal amino acid residues of 1.5 nmoles of a polypeptide, with a UV label provided by the alkylating reagent.

These and other objects and features of the invention will become more fully apparent when the following detailed description of the invention is read in conjunction with the accompanying drawing.

BRIEF DESCRIPTION OF THE DRAWINGS

FIGS. 1A–1D show the reaction of an alkylating agent with an peptidyl thiohydantoin (1A) to form an adduct-containing acyl thiohydantoin (1B), and cleavage of the thiohydantoin by reaction of the adduct-containing thiohydantoin with TFA, through a proposed intermediate (1C), to produce the cleaved, shortened peptide (1D);

FIGS. 2A–2D show the reaction of an alkylating agent with an peptidyl thiohydantoin (2A) to form an adduct-containing acyl thiohydantoin (2B), and cleavage of the thiohydantoin by reaction of the adduct-containing thiohydantoin with trimethylsilyl isothiocyanate (TMS-ITC), through a proposed intermediate (2C), to produce the cleaved, shortened peptide whose C-terminal amino acid has been converted to the corresponding acyl thiohydantoin;

FIGS. 5A–5C show possible resonance forms of an alkylated thiohydantoin after cleavage of an acyl thiohydantoin under acidic conditions;

DETAILED DESCRIPTION OF THE INVENTION

Figures 3A, 3B, 3C:
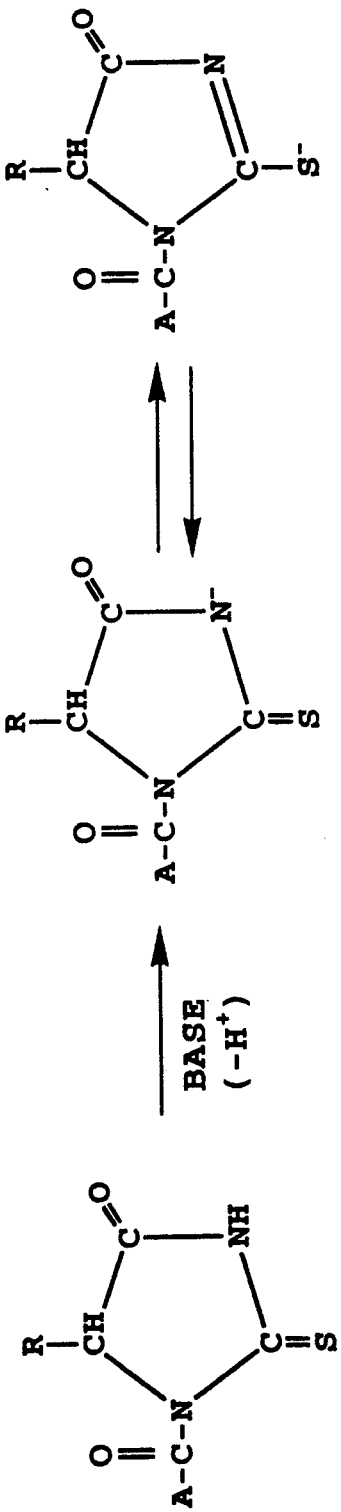
FIGS. 3A–3C illustrate deprotonation of an acyl thiohydantoin (3A) in a base, and the possible resonance forms of deprotonated acyl thiohydantoin (3B and 3C)

In practicing the method of the invention to accomplish C-terminal sequencing, the terminal carboxylic acid is first activated and then reacted to form a peptidyl thiohydantoin (Section A). The peptidyl thiohydantoin is caused to react, at a basic pH, with an alkylating agent which chemically modifies (alkylates) the thiohydantoin (Section B). The alkylated peptidyl-TH is treated with a cleaving agent under acidic conditions to cleave and release the modified C-terminal amino acid (Section C) from the peptide. The released, modified amino acid is separated and identified, for example by reversed-phase HPLC (Section D). The stepwise repetition (Section E) of activation, TH formation and modification, followed by cleavage and identification of the amino acid, provides a method of automated C-terminal for the sequencing of peptides and proteins.

Definitions of Terms

The term "peptide" or "polypeptide" refers to both peptides and proteins.

The term "thiohydantoin" or "TH" refers to the group as defined by formula I:

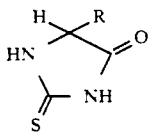

I shown here with the conventional numbering system for thiohydantoins. In the usual case, the thiohydantoin is formed from an amino acid, where R indicates the associated amino acid side chain. Alternatively, R may be any radical group whose electron withdrawing properties are similar to those of alkyl groups, including H, alkyl groups, and a variety of methylene linked R groups.

The term "acyl thiohydantoin" refers to the group defined by formula II below:

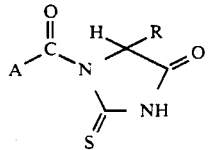

II where A represents a chemical group to which the thiohydantoin is attached via a carbonyl group. The identity of A is not critical provided that it does not interfere with thiohydantoin chemistry. Preferably, A is a peptide residue which can optionally be bound to a solid phase support through an internal or an N-terminal amino group.

When the thiohydantoin is formed from the C-terminal amino acid of a peptide, then AC(O)- moiety represents the remainder of the peptide other than the C-terminal amino acid and R is the side chain of the C-terminal amino acid and Formula I above is referred to as a C-terminal peptidyl thiohydantoin, where N' was the alpha-amino nitrogen of the original C-terminal amino acid, and $C^4$ was the carbon atom of the C-terminal carboxylate. Again, in this embodiment, the peptide can optionally be bound to a solid support through an internal or an N-terminal amino group.

The amide bond linking the AC(O) group to the thiohydantoin ring nitrogen N is referred to herein as an "acylthiohydantoin bond".

The term "reagent effective to alkylate the thiohydantoin so as to form the corresponding adduct of the thiohydantoin" refers to reagents of the formula III $X—R_2$  III wherein X is a leaving group, which under basic conditions, will be displaced by a group of the thiohydantoin so as to form an adduct. Preferably, X is a leaving group selected from chloro, bromo, iodo, tosyl, imidazolyl, and the like. $R_2$ is preferably a methylene R group of the form $—CH_2R'$, as exemplified by the $R_2$ groups given below, but may also be other groups, such as a methine of the form —CH—R'R".

Although the reagent $X-R_2$ is sometimes referred to herein as "the alkylating reagent", it is understood that this reagent is not limited to a strict definition of "alkyl", but is employed to recognize that this reagent forms a covalent bond between the thiohydantoin and the methylene group (—CH$_2$)— of the $R_2$ substituent. This $R_2$ group, when covalently bound to the thiohydantoin, is also referred to as an "adduct", and the modified or alkylated thiohydantoin, as an "adduct-containing", "modified", or "alkylated" thiohydantoin.

The specific label employed in $R_2$ is not critical provided that it is readily detectable by conventional means and is covalently bound, directly or indirectly, to the methylene group of the $R_2$ substituent attached to the sulfur atom of the modified thiohydantoin. The label is typically an fluorescent or other optical absorbing ring moiety, such as a benzyl or naphthyl group. The alkylating group may alternatively include a radioactive label, which would provide the most sensitive tag for TH detection. More generally the method of the invention allows a broad range of labels to be introduced, as part of the TH cleavage method.

Particularly preferred X-$R_2$ compounds containing a detectable label for use in this invention include, by way of example, the following compounds:

4-(bromomethyl)-phenylacetic acid phenacyl ester
Benzyl Bromide
Substituted Benzyl Bromides
i-Bromomethyl naphthalene
2-Bromomethyl naphthalene
Iodoacetamide
5-iodoacetamidofluorescein
6- iodoacetamidofluorescein
(((iodoacetyl)amino)methyl)fluorescein
4',5'-di(((iodoacetyl)amino)methyl)fluorescein
tetramethylrhodamine-5-(and-6)-iodoacetamide
rhodamine X iodoacetamide
eosin-5-iodoacetamide
erythrosin-5-iodoacetamide
Malachite Green iodoacetamide
7-diethylamino-3-((4,-iodoacetylamino)phenyl)-4-methylcoumarin
N-(1-pyrene)iodoacetamide
1-pyrenemethyl iodoacetamide
2-(4,-iodoacetamido)anilino)naphthalene-6-sulfonic acid
N-((2-iodoacetoxy)ethyl)-N-methyl)amino-7-nitrobenz-2-oxa-1,3-diazole
5-(2-((iodoacetyl)amino)ethyl)amino) naphthalene-1-sulfonic acid
4-acetamido-4'-(2-iodoacetyl)amino)stilbene-2,2'-disulfonic acid
Lucifer Yellow iodoacetamide
Cascade Blue TM aminoethyl iodoacetamide
4-iodoacetamidosalicylic acid
4-dimethylaminophenylazophenyl-4'-iodacetamide
benzophenone-4-iodoacetamide
N-(biotinoyl)-N'-(iodoacetyl)ethylenediamine
biocytin iodoacetamide
p-nitrophenyl iodoacetate
R-phycoerythrin, iodoacetylated
5-(bromomethyl)fluorescein
6-(bromomethyl)fluorescein
monochlorbimane
monobromotrimethylammoniobimane
N-(4-bromobutyl)phthalimide
N-(3-bromopropyl)phthalimide
N-(2-bromoethyl)phthalimide
N-(bromomethyl)phthalimide In all of these compounds, the atom designated as a specific halo can be a bromo, chloro, iodo or other suitable leaving group to provide for suitably labeled alkylating reagents for use in this invention.

The term "amino acid side-chain" means the group attached to the chiral carbon atom of the amino acid and is any substituent side-chains of naturally occurring, chemically modified or synthetically produced amino acids.

The term "substantially anhydrous" means a solution which contains less than about 0.5 weight percent water based on the total weight of the solvent. Preferably, substantially anhydrous acids will contain less than about 0.15 weight percent water. The particular substantially anhydrous acid or acid mimic employed is not critical but is preferably an acid selected from the group consisting of trifluoroacetic acid, hydrogen fluoride, thiocyanic acid, silyl triflate, silyl isothiocyanate, and the like. Acid mimics include silyl isothiocyanates [of the formula $R_xSi(SCN)_y$ wherein R is alkyl of from 1 to 6 carbon atoms, aryl of 6 to 10 carbon atoms, alkylaryl of 7 to 14 carbon atoms or any combination of these, x is an integer from 0 to 3, y is an integer from 1 to 4 with the proviso that the sum of x+ equals 4]. Silyl triflates are included as acids notwithstanding the fact that these compounds lack a proton because the groups are believed to mimic a proton in the process of this invention.

The term "solid support" or "solid phase support" refers to any solid support which contains surface functionality or can be derivatized so as to contain surface functionality which can interact with an amine group of a peptide so as to attach the peptide to the support directly or indirectly through the amine group of the peptide. Such attachment can be either by a covalent linkage or by ionic interactions or by hydrophobic interactions. Suitable solid supports include, but are not limited to, sepharose, amino-propyl silica, aminopropyl-CPG (controlled pore glass), aminoethyl cellulose, Tris-aryl ®-NH, glass beads, polyacrylamide particles, diisothiocyanate glass (DITC), and polystyrene.

A. Formation of an Acyl Thiohydantoin

Methods for the preparation of acyl thiohydantoins from the carboxyl group of either an amino acid or a C-terminal peptide are well documented in the literature. For example, in one general procedure for the preparation of such thiohydantoins, the carboxyl group is activated with an anhydride, such as acetic anhydride, in the presence of an isothiocyanate (ITC) salt or acid, to form a C-terminal peptidyl thiohydantoin via a C-terminal ITC intermediate (Stark). Other procedures for thiohydantoin formation include activation of the peptide with acetic anhydride (e.g., for 15 min at 50° C.) followed by reaction with trimethylsilyl isothiocyanate (e.g., for an additional 30 min at 50° C., Hawke); or reacting the carboxyl group of the C-terminal amino acid of a peptide with a mixed anhydride of isothiocyanic acid and a carboxylic, carbonic or sulfonic acid, under basic substantially non-aqueous conditions (Hawke).

A particularly preferred method for the preparation of the acyl thiohydantoin from the carboxyl group of the C-terminal peptide is by reaction with an in situ generated ketenimine followed by reaction with a silyl isothiocyanate (e.g., trimethylsilyl isothiocyanate). See Boyd et al., the disclosures of which are incorporated herein by reference.

The selected reaction procedure leads to the formation of the C-terminal peptidyl thiohydantoin wherein the C-terminal amino acid is converted to a C-terminal amino acid thiohydantoin which is linked to the next-in C-terminal amino acid in the peptide through an imide bond to a ring-nitrogen.

Exemplary alkylation reactions are detailed in Examples 1 and 2. Exemplary conditions for preparing a peptidyl-TH bound to a solid support are given in Examples 4 and 5.

B. Alkylation of the Thiohydantoin

This section describes the procedures employed to convert the thiohydantoin to a modified (alkylated) thiohydantoin. Specifically, the thiohydantoin is contacted with an alkylating reagent, $X-R_2$, which adds a group to the thiohydantoin producing a modified thiohydantoin. The reaction is generally conducted by employing either an equimolar amount or a molar excess of the alkylating agent relative to the thiohydantoin. When an excess of alkylating reagent is employed and when R is hydrogen (i.e., the C-terminal amino acid is glycine), it is contemplated that the alkylating agent can also react with and form a covalent link to the $C^5$ ring atom of the thiohydantoin.

Preferably, the reaction employs at least one molar equivalent of the tertiary amine and more preferably employs a substantial molar excess of the tertiary amine. The tertiary base is a trialkylamine having from 1 to 6 carbon atoms in each of the alkyl groups. Preferred trialkylamines include trimethylamine, triethylamine, diisopropylethylamine, and the like.

The reaction is conducted under substantially anhydrous conditions and at a temperature and reaction time sufficient to produce the desired alkylation of the thiohydantoin ring. A preferred temperature range is from about 30° to about 100° C. and a more preferred temperature range is from about 45° to about 60° C. The reaction is generally complete in from 0.1 to 1 hours.

Substantially anhydrous conditions are necessary because the modified thiohydantoin can react irreversibly with water to form a hydantoin, with release of an $SR_2$ group. Such hydantoins are neither readily cleaved by a substantially anhydrous acid nor readily reacted to form a thiohydantoin.

When the peptide is reacted in free form (i.e., unattached to a solid support and where the amino terminus is protected), the reaction is generally conducted in a liquid phase employing an inert solvent. Suitable inert solvents include, for example, acetonitrile, methylene chloride, chloroform, benzene, toluene, heptane, dimethylformamide, N-methylpyrrolidone and the like.

When the peptide is bound to a solid support, the alkylating reagent and the tertiary amine can be delivered in either a liquid or a vapor phase. When a liquid phase is employed, the reagents are generally mixed with an inert solvent which include, by way of example, acetonitrile, methylene chloride, chloroform, benzene, toluene, heptane, dimethylformamide, N-methylpyrrolidone and the like. When a vapor phase is employed, the alkylating reagent and the tertiary amine are generally mixed with an inert gas which include, by way of example, nitrogen, argon, and the like. Alternatively, it is contemplated that the alkylating reagent and the tertiary amine may be separately mixed with an inert gas and employed sequentially in the reaction. When employed in vapor phase delivery, the alkylating reagent and the tertiary amine are selected so as to provide for substantial vapor pressures at the reaction temperatures employed. A particularly preferred system includes trimethylamine as the base and as alkylating reagents, benzyl halides or derivatives thereof and cinnamyl halides (e.g., cinnamyl bromide) or derivatives.

When the peptide is in free form, the modified thiohydantoin product can be separated by filtration to remove the amine salt.

When the peptide is bound to a solid support, the modified thiohydantoin product can be isolated and purified by liquid washing with an inert solvent and/or gas purging with an inert gas. Suitable inert solvents and inert gases are as defined above. Alternatively, the solid support containing the peptide can be employed in the next step without any further isolation and/or purification.

Figures 4A, 4B:
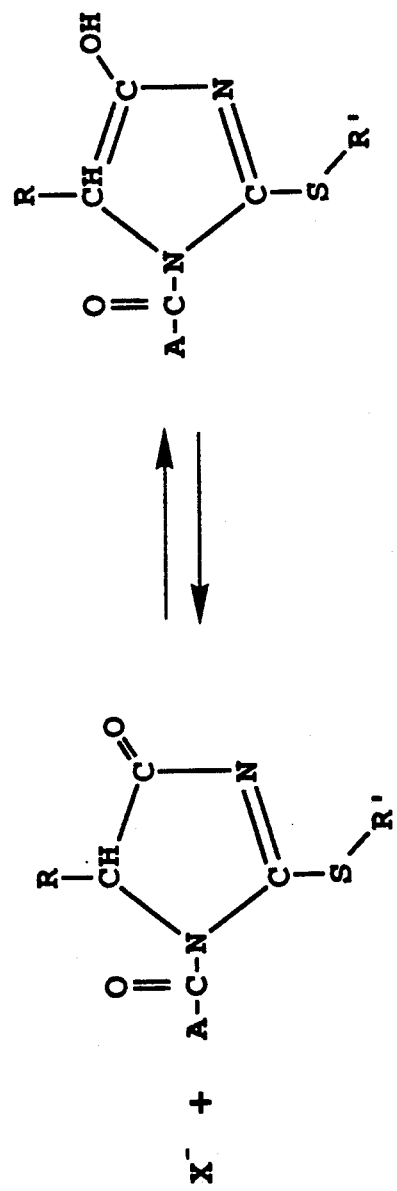
FIGS. 4A and 4B show reaction of the deprotonated acyl thiohydantoin (FIGS. 3B, 3C) with an alkylating agent (XR'), and possible resonance forms of the alkylated (adduct-containing) thiohydantoin (4A and 4B)

FIGS. 3A-3C and FIGS. 4A and 4B illustrate proposed reaction mechanisms for the above-detailed alkylating reaction. In FIGS. 3A-3C, an acyl thiohydantoin (3A) is deprotonated in a basic solution, leading to resonance forms (3B and 3C) which may favor electrophilic attack at either the ring N atom or the S atom. Preliminary NMR data indicates that alkylation is favored at the S atom. Alklyation at the S atom may also be favored by resonance stability due to possible resonance forms of the thioalkylated thiohydantoin, as seen in FIGS. 4A and 4B.

FIGS. 1A and 1B illustrate a thio-alkylation reaction in which a peptidyl thiohydantoin is alkylated with an $XR_2$ agent under basic conditions. Although the thio-alkylation reaction is illustrated, the possibility of alkylation at one or more thiohydantoin ring atoms (in addition to or as an alternative to thio-alkylation) cannot be ruled out. In any case, the alkylation reaction is effective to facilitate cleavage of the acyl-thiohydantoin bond, as discussed below, and the alkylation adduct attached to the thiohydantoin remains bound to the thiohydantoin after such cleavage.

Exemplary alkylation reactions are given in Examples 6 and 7.

C. Cleavage of the Modified Thiohydantoin

This section describes the cleavage step of the method of the invention, which involves treating the modified peptidyl thiohydantoin under acidic cleavage conditions effective to cleave the acyl thiohydantoin bond joining the modified thiohydantoin to an acyl group, e.g., the acyl group of the penultimate C-teminal amino acid of a peptide.

The cleavage conditions employ a molar excess of the cleaving agent. Such agents include trifluoroacetic acid, hydrogen fluoride, thiocyanic acid, silyl trifluoroacetate, trimethylsilyl trifluoromethanesulfonate (triflate), silyl isothiocyanate, and the like. Silyl isothiocyanates are of the formula $R_xSi(SCN)_y$ and silyl trifluoroacetate is of the formula $[CF_3C(O)O]_ySiR_x$, wherein R is alkyl of from 1 to 6 carbon atoms, aryl of 6 to 10 carbon atoms, alkylaryl of 7 to 14 carbon atoms or any combination of these, x is an integer from 0 to 3, y is an integer from 1 to 4 with the proviso that the sum of $x+y$ equals 4.

The cleavage reaction is typically carried out at a temperature from about 20° C. to about 60° C., and typically for a reaction time of about 0.1 to 2 hours. The course of the reaction can be readily followed by examining the cleaved product and/or shortened peptide, according to analytical methods described below.

When the peptide is reacted in free form (i.e., unattached to a solid support and where the amino terminus is protected), the cleavage reaction is generally conducted in a liquid phase employing an inert solvent. Suitable inert solvents include, for example, acetonitrile, methylene chloride, chloroform, benzene, toluene, heptane, and the like. In this format, the remaining peptide can be isolated and purified by conventional means including concentration under reduced pressure, distillation, chromatography, and the like.

When the peptide is bound to a solid support, the cleavage reagent is delivered in either a liquid or a vapor phase. When a liquid phase is employed, the reagent is generally mixed with an inert solvent which include, by way of example, acetonitrile, methylene chloride, chloroform, benzene, toluene, heptane, and the like. When a vapor phase is employed, the cleavage reagent is generally mixed with an inert gas which include, by way of example, nitrogen, argon, and the like. In this embodiment, the cleavage reagent is selected so as to provide for substantial vapor pressures at the reaction temperatures employed. In this format, the remaining peptide can be isolated and purified by liquid washing with an inert solvent and/or gas purging with an inert gas. Suitable inert solvents and inert gases are as defined above.

Studies carried out in support of the present invention show that above cleavage conditions are effective to cleave the acyl-thiohydantoin bond involving a modified thiohydantoin, with the reaction going to completion or near completion. By contrast, an unmodified thiohydantoin is not cleaved or cleaved only poorly under the same reaction conditions.

FIGS. 1B-1D illustrate proposed steps in a acyl thiohydantoin cleavage reaction carried out on a peptidyl thiohydantoin as part of a C-terminal sequencing reaction. Here the thiohydantoin is formed from the C-terminal amino acid, with the thiohydantoin R group representing the amino acid side chain, and the acyl-thiohydantoin bond being formed between the thiohydantoin and the carbonyl group of the next-in (penultimate) amino acid sequence (having a side chain R').

Treatment of the peptidyl thiohydantoin with substantially anhydrous trifluoracetic acid (TFA) releases the thiohydantoin, with possible formation of an unstable mixed anhydride intermediate (FIG. 1C). In the presence of trace amounts of water, the intermediate would be quickly hydrolysed to form the carboxylic acid group of the next-in amino acid residue (FIG. 1D).

In one preferred cleavage method, especially for use in C-terminal sequencing, the acyl thiohydantoin is cleaved by a mixture of trifluoroacetic acid and silyl isothiocyanate or by the addition of a silyl isothiocyanate followed by addition of trifluoroacetic acid. Under these conditions, the trifluoroacetic acid may form an intermediate mixed anhydride of trifluoroacetic anhydride (FIG. 2C) which rapidly reacts with silyl isothiocyanate to form an acylisothiocyanate which cyclizes to form the thiohydantoin of the next-in amino acid (FIG. 2D).

Alternatively, the trifluoroacetic acid may serve to catalyze the reaction of the silyl isothiocyanate in cleaving the acyl thiohydantoin bond and forming the thiohydantoin group of the next-in amino acid.

This method is preferred because both reagents can be optionally delivered in the gas phase; this form of the method avoids the use of liquid solvents and the inadvertent inclusion of water, which can irreversibly convert the modified thiohydantoin to the hydantoin or non-alkylated thiohydantoin, and also cleave off the modified thiohydantoin (forming a C-terminal acid group).

It is contemplated that other acids such as anhydrous HF (gas phase) can be used in place of trifluoroacetic anhydride in such a mixture with the silyl isothiocyanate so as to both cleave the modified thiohydantoin on the C-terminal amino acid and to form a thiohydantoin with the next-in amino acid.

One reason for the enhanced TH cleavage achieved in the present invention may be related to imidazole-like TH structure which may be formed on alkylation. This feature is illustrated in FIGS. 4A and 4B, which shows two possible resonance forms of th alkylated TH. The form shown in FIG. 4B resembles an imidazole which is known to be a good leaving group.

The cleavage reaction may be further enhanced by increased stability of the released thiohydantoin. As seen in FIGS. 5A-5C, the cleaved, alkylated thiohydantoin has the requisite 6 pi electrons needed for aromaticity, thus enhancing the stability of the released compound, and lowering the energy of the transition state leading to its formation.

Although, as indicated above, the structure of the cleaved modified thiohydantoin containing the C-terminal amino acid is not known with certainty, it is known that when the $R^2$ group contains a detectable label, this label remains bound to the C-terminal amino acid cleaved from the peptide. Because the $R_2$ group remains with the C-terminal amino acid, the use of a detectable label in the $R_2$ substituent permits facile detection of the cleaved amino acid.

D. Identification of Modified Amino Acid TH

The cleaved product containing the amino acid released from the peptide or the shortened peptide can be analyzed to identify the C-terminal amino acid. Where the peptide is coupled to a solid support, the cleaved product released from the peptide can be easily separated by removing the cleavage-reaction solvent, e.g., by vacuum centrifugation, and extracting the cleaved product in a suitable solvent such as acetonitrile, as detailed in the Examples hereinbelow. Where the peptide is free in the cleavage reaction mixture, the mixture may be separated, by suitable means as known in the art e.g., by RP-HPLC, ion-exchange chromatography or capillary electrophoresis, as part of the method for identifying the compound.

The HPLC method detailed in Example 11 is one which is suitable for identification of cleaved, modified amino acids by comparison with reference standards. FIGS. 7-9 are HPLC profiles of amino acid containing cleaved products obtained after several rounds of C-terminal sequencing, as described below.

E. C-Terminal Amino Acid Sequencing

The method described in Sections A-D above can be employed for determining the C-terminal amino acid residue of a peptide. It will be appreciated that repeated application of the method can be used for C-terminal amino acid sequencing of the peptide.

Figure 6:
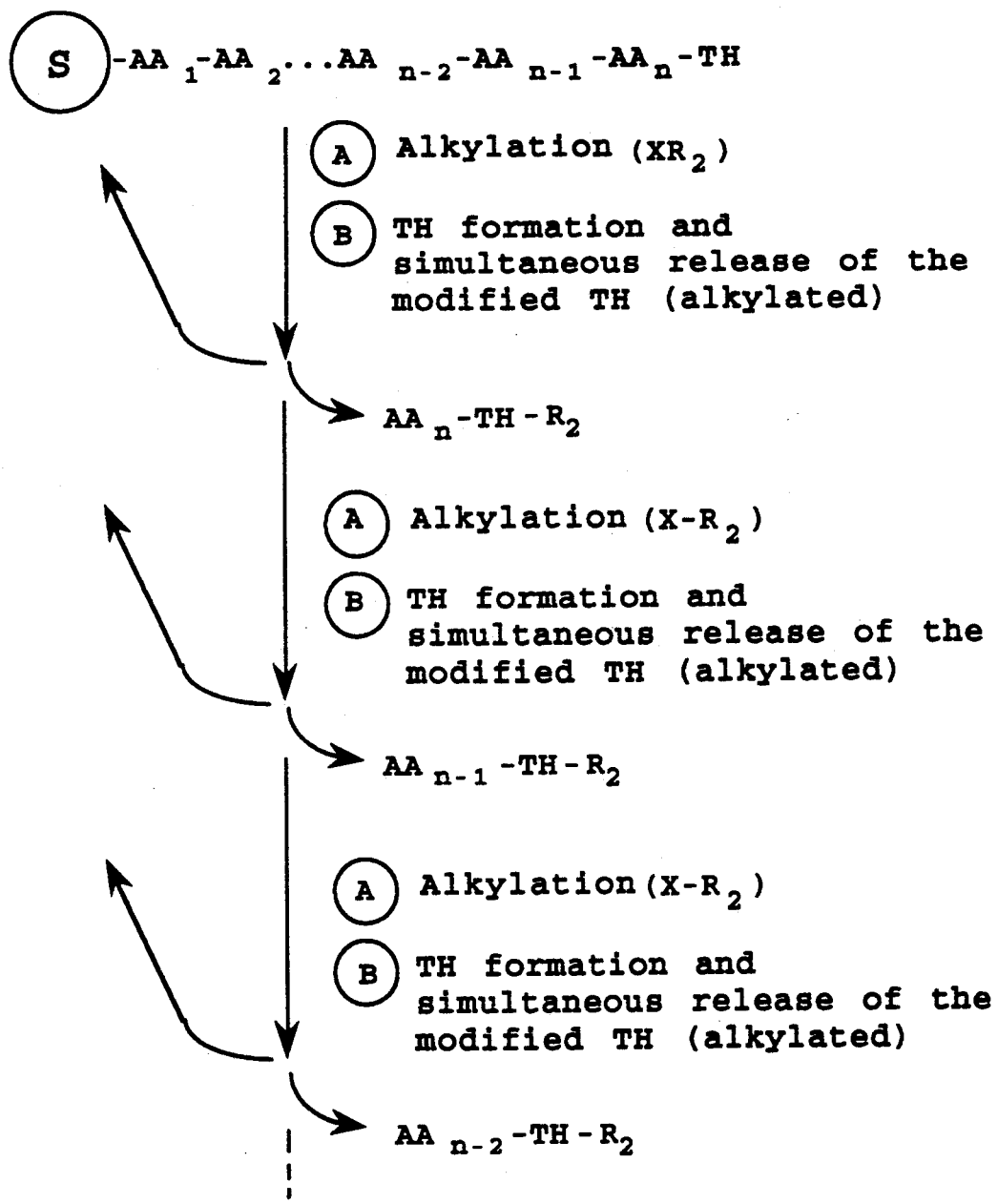
FIG. 6 illustrates the reaction sequences for a preferred method of conducting C-terminal amino acid sequencing of a peptide by this invention.

FIG. 6 illustrates a preferred sequencing method. The peptide to be sequenced is coupled to a solid support, S, as indicated. The peptide is then carried through a first round of steps to (a) produce the C-terminal peptidyl thiohydantoin containing the terminal amino acid ($AA_n$-TH), (b) alkylate the C-terminal peptidyl thiohydantoin, and (c) cleave the terminal modified thiohydantoin, yielding a cleaved product containing the C-terminal amino acid ($AA_n$-TH-$R_2$) and a shortened peptide whose C-terminal residue is now $AA_{n-1}$. The released thiohydantoin is captured for identification, e.g., by HPLC.

After washing the peptide support, the shortened peptide is subjected to second round of the above steps to release the next-in amino acid as part of the cleaved product ($AA_{n-1}$) and yield a peptide shortened by two C-terminal residues. This procedure is repeated until the peptide has been sequenced or until loss of resolution makes further sequencing impossible.

In a preferred embodiment, the cleavage of the C-terminal amino acid is coupled with the formation of the thiohydantoin of the next-in amino acid. In this embodiment, the cleaving agent is selected from the group consisting of thiocyanic acid, silyl isothiocyanate, and a mixture of a substantially anhydrous acid and silyl isothiocyanate.

The above-detailed technique is easily automated using technology known for the automated sequencing of the N-terminal residues of peptides. One embodiment of a device to automatically sequence a peptide from the C-terminal end employs a solid support contained in a reaction vessel to which fresh solvent and reagents are added, and from which reaction mixtures and solvent washes are removed. The released amino acid isothiocyanates are extracted from the support and transferred to an on-line RP-HPLC for analysis.

Automated C-terminal sequencing reactions carried out in accordance with the invention have allowed sequencing of five C-terminal residues in two proteins (Examples 11 and 12) which were examined (only five rounds were carried out in each case), and sequencing of ten C-terminal residues in a synthetic peptide (Example 13) where the sequencing was taken to the limit of resolution.

From the foregoing, it can be appreciated how various objects and features of the invention are met. The initial alkylation reaction can be employed to couple a label to the thiohydantoin, for use in detection of the released thiohydantoin product, e.g., by HPLC.

The TH cleavage reaction can be carried out under mild conditions which reduce unwanted modification of peptide side chains. At the same time, the reaction is efficient and can be taken to completion or near completion rapidly, perhaps due in part to the imidazole-like TH formed on alkylation and/or because of the enhanced stability of the aromatic TH ring which is released.

The cleavage reaction can be coupled to the formation of the thiohydantoin of the next-in amino acid, thus rendering repetitive C-terminal amino acid analysis more efficient which allows sequencing to be carried out quickly in an automatic system. Further, the method is readily adapted to automated sequencer operation.

The combined advantages allow significant increase in the number of C-terminal residues which can be determined. The ability to sequence 5-10 C-terminal residues on only 1.5-3.6 nmoles protein, as detailed in Examples 11-13 below, represents a significant advance over other methods available heretofore.

The following examples are offered to illustrate this invention and are not to be construed in any way as limiting the scope of this invention.

In these examples, the following abbreviations are defined as follows (if not defined, the abbreviations have their generally accepted meanings):

| | |
|---|---|
| AAA | Amino Acid Analysis |
| "BS³" | sulfosuccinimidyl suberate |
| Boc or t-BOC | t-butoxycarbonyl |

| | |
|---|---|
| BITC | benzoylisothiocyanate |
| CD₃CN | deuterium substituted acetonitrile |
| CPG | Controlled Pore Glass |
| "DSS" | disuccinimidyl suberate |
| FMOC | fluorenylmethoxycarbonyl |
| HPLC | High Performance Liquid Chromatography |
| ITC | isothiocyanate |
| MeCN | acetonitrile ($CH_3CN$) |
| MeOH | methyl alcohol ($CH_3OH$) |
| NMP | N-methylpyrrolidone |
| NMR | $^1$H Nuclear Magnetic Resonance Spectroscopy |
| "Sparrow Resin" | A Polyacrylamide resin, prepared by Dr. Sparrow |
| TEA | triethyl amine |
| TFA | trifluoroacetic acid or trifluoroacetate |
| TH | thiohydantoin |
| TLC | thin layer chromatography |
| TMS—N=C=S or TMS—ITC | trimethylsilyl-isothiocyanate (($CH_3)_3SiNCS$) |
| WRK | Woodward's Reagent K (2-Ethyl-5-phenylisoxazolium-3'-sulfonate) |

Materials

In the these examples, pyridine, methylene chloride, acetonitrile, triethylamine, benzenesulfonyl chloride, trimethylsilyl ITC, and benzoyl ITC were obtained from Aldrich Chemical Co. (Milwaukee, Wis.). Leucine enkephalin was from Sigma Chemical Company (St. Louis, Mo. 63178). Other peptides, N-acetyl-peptides, protected and de-protected amino acids were from either obtained from Bachem Biosciences Inc.(Philadelphia, Penna.) or prepared by standard methods at ABI. Nuclear magnetic resonance spectra were collected on a Varian 300.

EXAMPLE 1

A. Preparation of t—Boc—Leu—TH

Five mmole of t—Boc—Leu was dissolved in 25 mL of acetonitrile. One equivalent plus 10% excess of ethoxycarbonylisothiocyanate (5.5 mmole, 0.649 mL) and two equivalents of pyridine (10 mmole, 0.833 mL) were added. The reaction mixture was stirred for two hours at room temperature. Solvent was removed by rotary evaporation and the resultant oil was purified using column chromatography on silica gel, with elution in $CH_2Cl_2:C_3OH$ (9:1). The purified, Boc-protected Leu thiohydantoin was characterized by $^1$H NMR spectroscopy (Instrument: 300 MHz Varian, Solvent $CD_3CN$); the characteristic peaks were: 9.7 (—N—H—proton), 4.49 (—CH— ring), 187-1.74 (—CH₂—), 0.86 (CH₃—), and 0.88 (CH₃—).

B. Preparation of Leu-TH Reference Standard

Leu thiohydantoin was prepared from t-Boc Leu, obtained as above, by removal of the Boc protecting group. Treatment with either anhydrous or aqueous (25%) TFA at 60° C. for 30 minutes was sufficient to remove all N-protection. The Leu-TH was analyzed by NMR, as above, and the characteristic peaks were: 9.35 (-NH-proton), 8.05 (—NH—) 4.16 (—CH— ring), 1.78 (—CH— sidechain), 1.58

EXAMPE 2

Preparation of a Peptidyl-TH

A. Preparation of Model Peptides

Test peptides were synthesized using an ABI Model 431A Peptide Synthesizer with the standard ABI Fastmoc ™ reaction cycles, for the 0.25 mmole scale. Final de-protection, cleavage and purification were by standard methods. Products were characterized both by HPLC and Amino Acid Analysis.

Test Peptide Sequences:

"GAPFLY": Fmoc-GlyAlaProLysGlyLysGlyLysTyrPheLeuTyr
"A14G": Fmoc-AlaLysGlyLysGlyLysLeuPheTyrGlyLeuPheTyrGly
"A14L": Fmoc-AlaLysGlyLysGlyLysGlyPheTyrLeuGlyPheTyrLeu
"A15G": Fmoc-AlaLysGlyLysLeuTyrPheGlyLeuTyrGlnPheGly
Leucine Enkephalin: TyrGlyGlyPheLeu

B. Preparation of Acetyl-AlaAlaAla-TH 0.2 g (0.73 mmole) of acetyl-AlaAlaAla was suspended in 25 mL of $CH_3CN$. Two equivalent pyridine (0.12 mL) and two equivalent ethoxycarbonylisothiocyanate (0.2 mL) were added and the mixture was stirred overnight, producing a clear, homogeneous solution. The solvent was partially removed by rotary evaporation, producing an oil. Acetyl-AlaAlaAla-TH was purified from the oil by column chromatography on silica gel, with elution in $CH_2Cl_2:CH_3OH$ (9.2:0.8). The purified peptidyl thiohydantoin was characterized by H NMR spectroscopy (Instrument: 300 MHz Varian, Solvent: $CD_3CN$); the characteristic peaks were: 6.02 (1H α proton, middle Ala), 4.6 (—CH— ring), 4.3 (α proton, Ala), 1.88 (acetyl CH₃- proton) 1.42, 1.32, 1.2 (3 sets of Ala CH₃—).

Note: the downfield shift observed for the middle Ala α proton (~4.3 to 6.0), was attributed to a deshielding anisotropy effect caused by the neighboring C=S of the thiohydantoin ring.

EXAMPLE 3

Preparation of Peptide Attached to a Solid Support

A. Preparation of Peptide Attached to Sparrow Resin 10 mg Sparrow Resin (7 mequiv. NH₂/mg resin) was placed in a 1 mL capped tube with 0.5 mL of CH:CN containing 10% TEA and allowed to swell for 10 min. The liquid was removed and the resin washed first with 0.5 mL $CH_3CN$ followed by 0.5 mL N-methyl-pyrrolidine ("NMP"). 12 mg (3 equivalent/amine of resin) of the bifunctional crosslinking reagent, sulfosuccinimidyl suberate ("BS³"), was dissolved into 50 μL NMP-10% TEA. The pre-dissolved solution of BS³ was added to the washed resin, and after 10 minutes, 5 μL proceed for 1-2 hours at room temperature, with occasional of pyridine was added, and the reaction was allowed to agitation. The resin was then washed three times, each with 0.5 mL NMP. The peptide, (from ~1-3 equivalent/resin amine) in 0.5 mL of NMP-10% pyridine, was added and allowed to react overnight, at room temperature, with shaking. The resin was then washed, twice each with 0.5 mL NMP, H₂O and $CH_3CN$, and dried under vacuum in a Savant Speed-Vac. The attachment yield was determined by amino acid analysis and/or Fmoc-piperidine assay. The usual yields varied between ~20-100 nmole peptide/mg resin.

B. Preparation of Peptide Attached to CPG Glass Beads 100 mg Controlled Pore Glass beads ("CPG") (1000Å, 40 μmole amine/g bead) was placed in a capped 1 mL eppendorf tube. 15 mg (10 equivalent/resin amine) of the bifunctional crosslinking reagent, disuccinimidyl suberate ("DSS"), was dissolved into 400 μL NMP containing 5–10% TEA. The pre-dissolved solution of DSS was added, after 10 minutes 5 μL of pyridine was added, and the reaction was allowed to proceed for 1–2 hours at room temperature. The glass beads were then washed three times, each with 0.5 mL NMP. The peptide (1 equivalent) in 0.3 mL of NMP-10% pyridine was added and allowed to react overnight, at room temperature, with shaking. The resin was then washed with NMP, $H_2O$ and $CH_3CN$ and dried under vacuum in a Savant Speed-Vac. The attachment yield, determined by amino acid analysis, typically was 1 nmole peptide/mg bead.

EXAMPLE 4

Preparation of a Peotidtl-TH Attached to a Solid Support

Ketenimine was generated in solution by suspending 62 mg (0.25 mmole) Woodward's Reagent K ("WRK": 2-Ethyl-5-phenylisoxazolium-3,-sulfonate) in 2 mL $CH_3CN$ and adding 50 μL (one equivalent, 0.25 mmole) of diisopropylethyl amine ("DIEA"). The suspension was monitored until it became a clear yellow solution (~15 min.) and then used.

Peptide attached to a solid support (resin or glass bead) was prepared, as described above, in Example 3. 10–100 mg of solid support, containing ~0.1–1.0 μmole peptide was mixed 0.5 mL of the freshly generated ketenimine solution from above in a 1 mL capped eppendorf tube. The mixture was allowed to react for 4 hours at room temperature with continual shaking. The solid support was then rinsed three times with $CH_3CN$.

0.5 mL of 10% TMSITC in $CH_3CN$ was added to the peptide on the solid support, with the activated carboxylate group generated above. The reaction vessel was again capped and stored overnight at room temperature. The solid support was then washed with $CH_3CN$, NMP, $H_2O$ and again with $CH_3CN$, and dried under vacuum in a Savant Speed-Vac.

EXAMPLE 5

Modification of Leu-TH with PAM Linker

Two g (0.0074 mole) t-BocLeuTH, prepared as in 1A above, was dissolved in 10 mL $CH_3CN$. One equivalent of 4-(bromomethyl)-phenylacetic acid phenacyl ester, "PAM" Linker (2.2 g, 0.0074 mole), and one equivalent TEA (1 mL, 0.0072 mole) were added. The reaction mixture was heated to about 60°–80 ° C. for 8 min., then stored at −20° C. overnight. A precipitant of TEA.HBr was removed by filtration, and the supernatant was concentrated under reduced atmospheric pressure, resulting in the formation of an oil. The oil was treated with TFA (100%) at 50 ° C. for 45 min. The subsequent complete removal of TFA produced a white solid. The solid was dissolved and purified using column chromatography on silica gel, with elution in $CH_2Cl_2$:$CH_3OH$ (9:1), the product displayed a rf of about 0.5. The purified material was analyzed by NMR, as above, and the characteristic peaks were: 7.89–7.23 (aromatics), 5.34 ($O—CH_2—C=O$) 4.34 ($O—CH_2—Ar$), 4.1–3.9 (CH-ring), 3.74 ($Ar—CH_2C—O$), 1.9–1.6 (sidechain —CH— and —$CH_2$), 0.905 (two $CH_3$—).

EXAMPLE 6

Modification of a Peptidyl TH with Ethylbromoacetate 100 mg (0.31 mmole) acetyl-AlaAlaAla-TH was prepared as described in Example 2, and dissolved in 1 mL acetonitrile. One molar equivalent (36.8 μL) of ethylbromoacetate was added with one equivalent (43.7 μL) TEA; the reaction was allowed to proceed for 10 minutes at 60° C. The reaction mixture was placed at −20° C. overnight. A precipitant of TEA·HBr was removed by filtration, and the supernatant was concentrated under reduced atmospheric pressure, resulting in the formation of an oil. The oil was analyzed by H NMR and characterized as the acetyl-$(Ala)_2$-Ala-TH-ethylacetate-adduct: 4.7–4.15 (α protons, Ala), 4.15 ($O—CH_2—$), 3.85 ($S—CH_2—C=O$) 1.85 (acetyl $CH_3$—) 1.6, 1.5, 1.3 (3 sets of Ala $CH_3$—) 1.15 ($O—CH_2CH_3$).

Note: the loss of the previously observed downfield shift (6.0) of the middle Ala o proton, which was attributed to a neighboring C=S.

Note: the results also contained complicating resonance signals from isomers of the TH starting material and residual TEA (triethylamine).

EXAMPLE 7

Modification of a Peptidyl TH with Benzyl Bromide

The procedure described in Example 6 was followed substituting one molar equivalent of benzyl bromide in place of the ethylbromoacetate. The product was analyzed by $^1H$ NMR and characterized as the acetyl-$(Ala)_2$-Ala-TH-benzyl-adduct: 7.55–7.1 (aromatics), 4.8–4.2 (α protons, Ala), 4.35 (S-$CH_2$-Ar), 1.85 (acetyl $CH_3$—) 1.6, 1.5, 1.3 (3 sets of Ala $CH_3$—).

It is noted that the results also contained complicating resonance signals from isomers of the TH starting material and residual TEA.

Modification of peptidyl thiohydantoins can also be achieved by use of different alkylating reagents by mere substitution for the alkylating reagents recited above. Preferably, such reagents have a label so as to provide facile detection of the cleaved product.

EXAMPLE 8

Cleavage of the Modified C-terminal Amino Acid with TMSITC

Acetyl-AlaAlaAlaTH-benzyl was prepared as described above in Example 7 and dissolved in $CD_3CN$, to allow NMR monitoring of the reactants and products. A few drops of TMSITC were added and the mixture heated at 60° C. for 1.5 hours. NMR spectra were obtained and compared with those of known species acetyl-AlaAla-TH and AlaTHbenzl-adduct. Results were consistent with the presence of both the acetyl-AlaAla-TH and AlaTHbenzl-adduct. Acetyl-AlaAla-TH: 6.08 (α proton, Ala), 1.8 (acetyl $CH_3$—), 1.43, 1.32 (Ala $CH_3$—); AlaTH-benzl-adduct: 4.6 (—$CH_2$—Ar), 4.5 (—CH—), 1.5 (Ala $CH_3$—).

EXAMPLE 9

Cleavage of the Modified C-terminal Amino Acid with TMSITC/TFA

Acetyl-AlaAlaAlaTH-benzyl was prepared and treated as described above in Example 8, except that a few drops of TFA were also added into the mixture. The monitoring with NMR showed that after 10 minutes at 60° C. the predominant species were the acetyl-AlaAla-TH and the AlaTHbenzl-adduct.

EXAMPLE 10

Cleavage of the Modified C-terminal Amino Acid with TFA

Acetyl-AlaAlaAlaTH-benzyl was dissolved directly in anhydrous TFA and heated at 60° C. for 10 minutes. The TFA was removed by use of a Savant Speed-Vac and the material dissolved in $CD_3CN$ for NMR analysis. The anticipated signals were seen.

These results are summarized in Table 1 and it can be seen that cleavage proceeded to completion within about one hour for those $R_2$ substituents other than methyl but there was no cleavage when $R_2$ was methyl

TABLE 1

| $R_2$ | cleaving agent(s) | cleavage after 1 hour at 60° C. |
|---|---|---|
| $-CH_2C_6H_4NO_2(p)$ | TFA or TMS—N=C=S | INCOMPLETE |
| $-CH_3$ | TMS—N=C=S | NONE |
| $-CH_2C(O)NH_2$ | TMS—N=C=S | COMPLETE |
| $-CH_2C(O)OC_2H_5$ | TMS—N=C=S | COMPLETE |
| $-CH_2C_6H_5$ | TMS—N=C=S | COMPLETE |
| PAM[1] | TFA or TMS—N=C=S | COMPLETE |

[1] 4-(bromomethyl)-phenylacetic acid phenacyl ester

EXAMPLE 11

Automated C-Terminal Sequencing of Apomyoglobin

This example demonstrates the use of the method to determine the C-terminal amino acid sequence of five terminal amino acids of apomyoglobin. In this method 4.3 mgs of apomyoglobin (about 3.6 nmole) attached to DITC glass, was purchased from Sigma. The amino acid sequence of the five C-terminal residues is:

R-LeuGlyPheGlnGly.

The C-terminal carboxyl group was reacted in a manner similar to that of Example 4, to form the thiohydantoin.

A. Peptide Activation, Modification and Terminal Amino Acid Cleavage

The C-terminal thiohydantoin of this peptide was then subjected to amino acid sequencing from the C-terminal direction by using a ABI Model 477 pulsed-liquid gas-phase Automated Sequencer followed by cleavage of the modified thiohydantoin with substantially anhydrous TMS-ITC.

The material was subjected to cleavage cycles as regulated by an optimized program whose steps are outlined below. The cleaved material was transferred to an on-line HPLC for analysis of the amino acid adduct. The entire elapsed time to conduct the necessary steps to cleave the C-terminal amino acid (as part of the modified thiohydantoin) was approximately 1 hour.

In the cycle, as directed by the program, the support containing the peptidyl-TH was wetted with 10% DEA in MeCN, then flushed with argon to remove the MeCN. The alkylating reagent, 1-(bromomethyl)-naphthalene was added in 1:1 MeCN/NMP, then the support was flushed with argon to remove the MeCN, and the system was allowed to react for 10 minutes at 60° C. The process was repeated to ensure modification of all TH groups. Residual reactants were washed out of the system with MeCN, followed by argon flushes to remove the MeCN.

The modified peptidyl-TH on the support was treated with 10% TMS-ITC in substantially anhydrous MeCN, then with neat TFA, vapor phase, to catalyze the cleavage of the alkylated C-terminal amino acid TH. After 15 minutes reaction time, the cleaved amino acid derivative was washed from the support with 100% MeOH in water, and transferred to an HPLC for separation and identification.

B. HPLC Separation and Identification

The separation of the modified amino acid-TH were achieved using an on-line HPLC system (Model 120A, ABI), equipped with a narrow-bore column (C-18, ABI PTC-column 220×2.1 mm, 5 micron). The flowrate was 300 uL / min with an operating pressure of 2000 psi. A gradient elution was used with a two-solvent system: solvent A=50 mM sodium acetate, pH 5.4, solvent B=90% (vol/vol) acetonitrile in 10% solvent A. After a 12 minute equilibration at 7% B, the sample was injected onto the column and the solvent was delivered for 20 minutes in a linear gradient to 60% B. Solvent composition was then ramped to 100% B in 5 minutes, and held isocratically for 5 more minutes. Effluent was monitored at 254 nm.

Figure 7A:
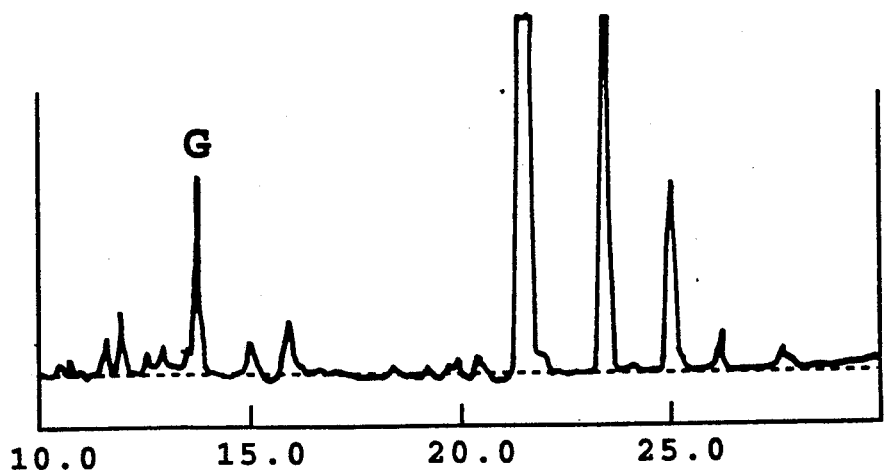
FIGS. 7A–7E show HPLC chromatograms of the first-fifth cycles, respectively, in the C-terminal sequencing of 3.6 nmoles apomyoglobin.
Figure 7B:
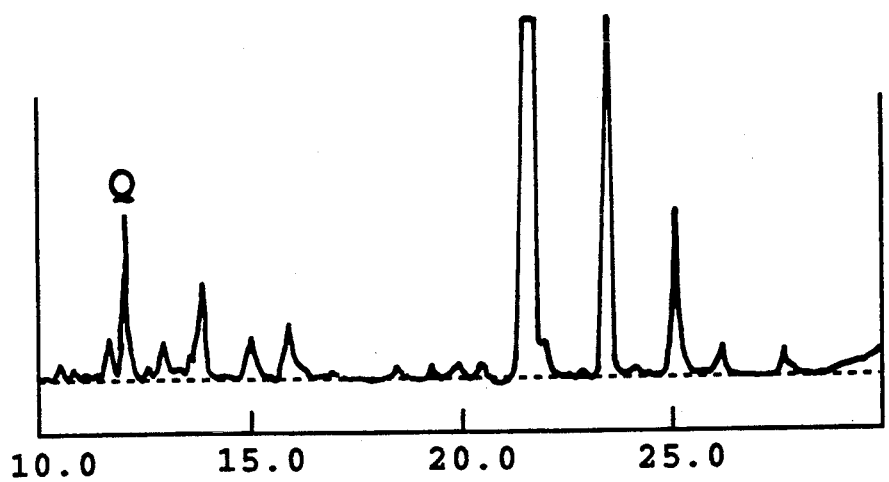
Figure 7C:
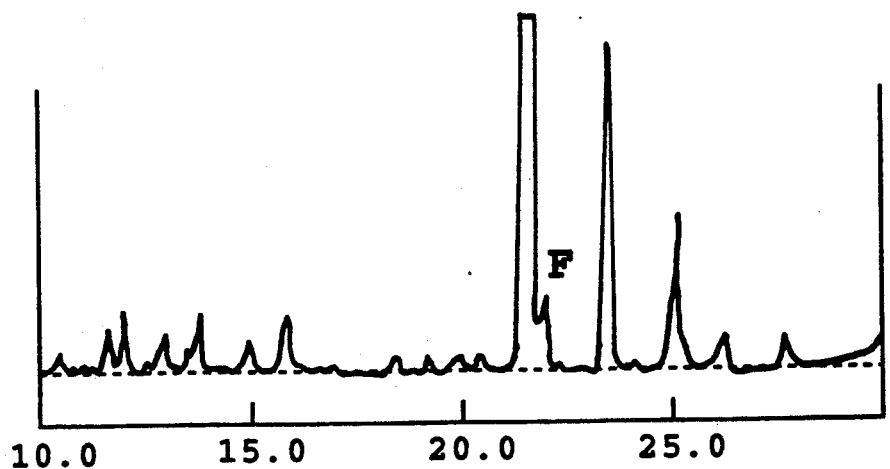
Figure 7D:
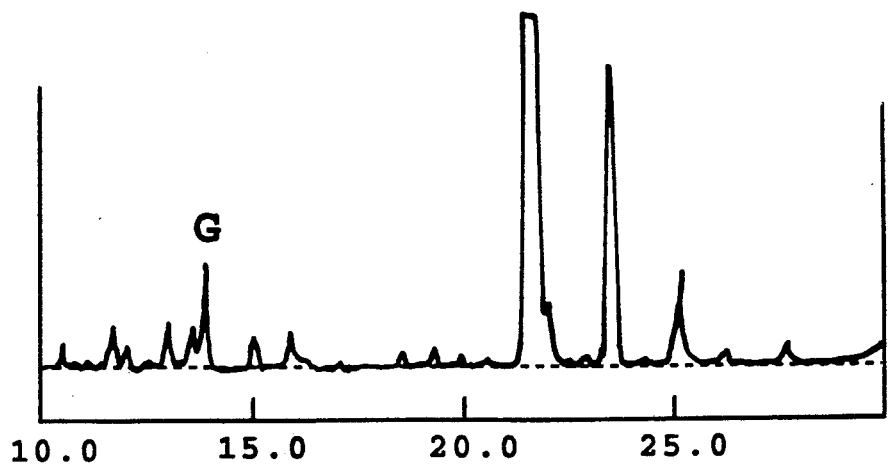
Figure 7E:
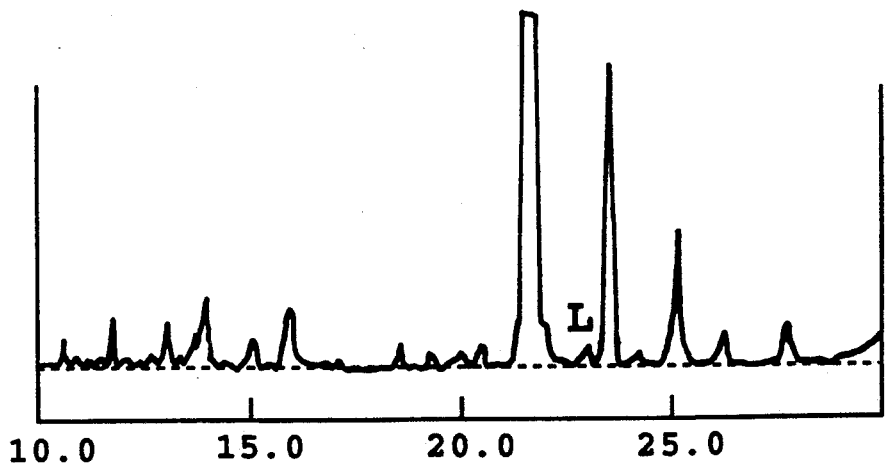
Figure 8A:
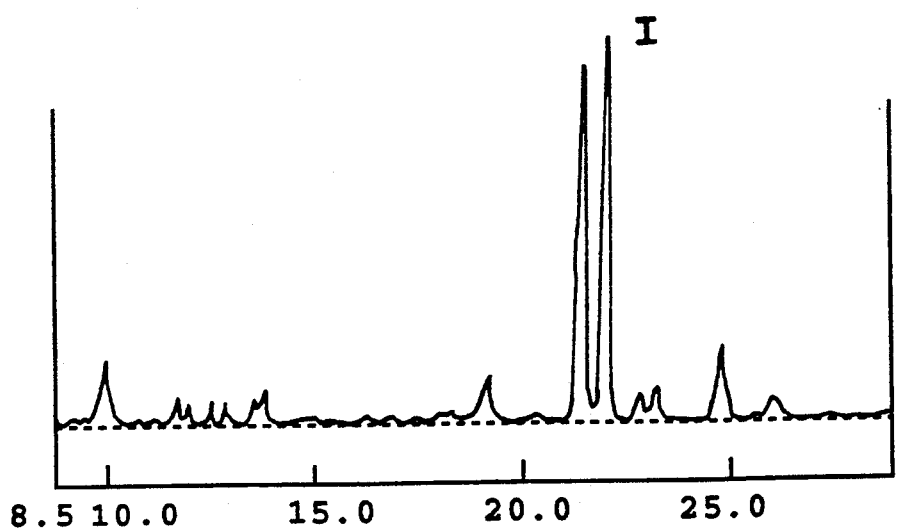
FIGS. 8A–8E show HPLC chromatograms of the first-fifth cycles, respectively, in the C-terminal sequencing of 1.5 nmoles β-lactalbumin.
Figure 8B:
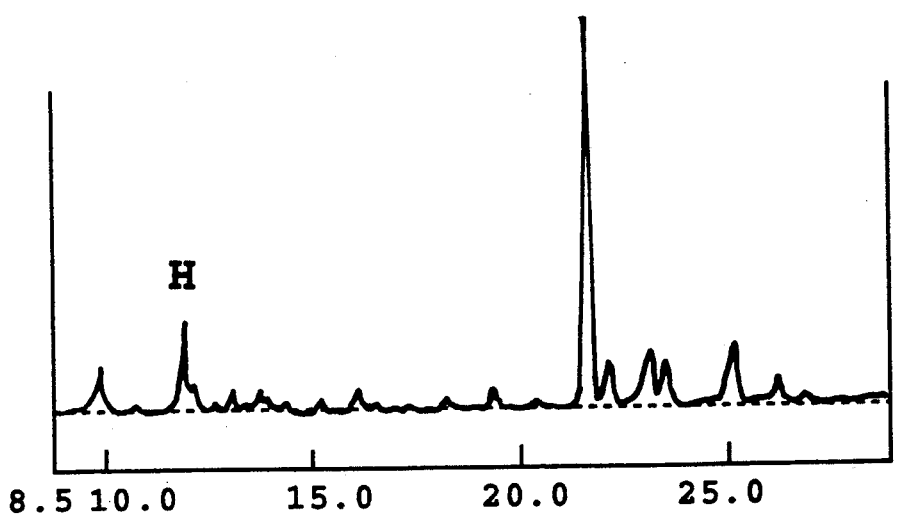
Figure 8C:
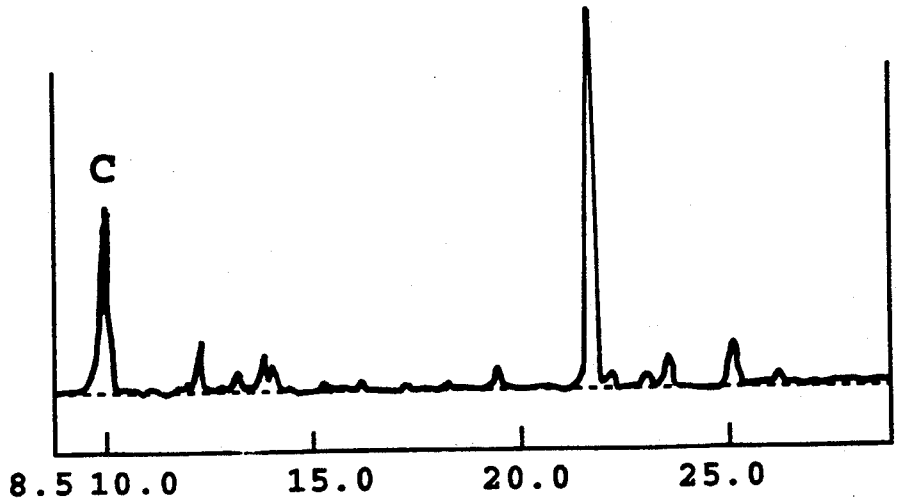
Figure 8D:
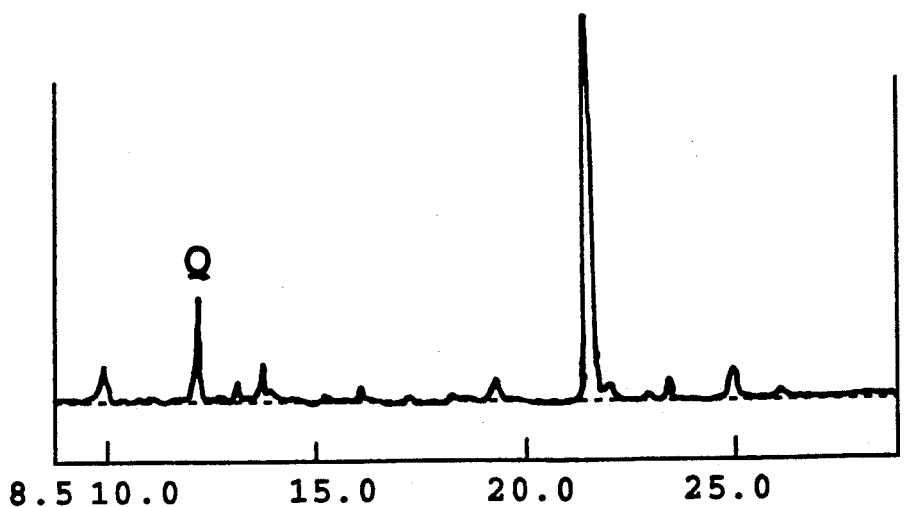
Figure 8E:
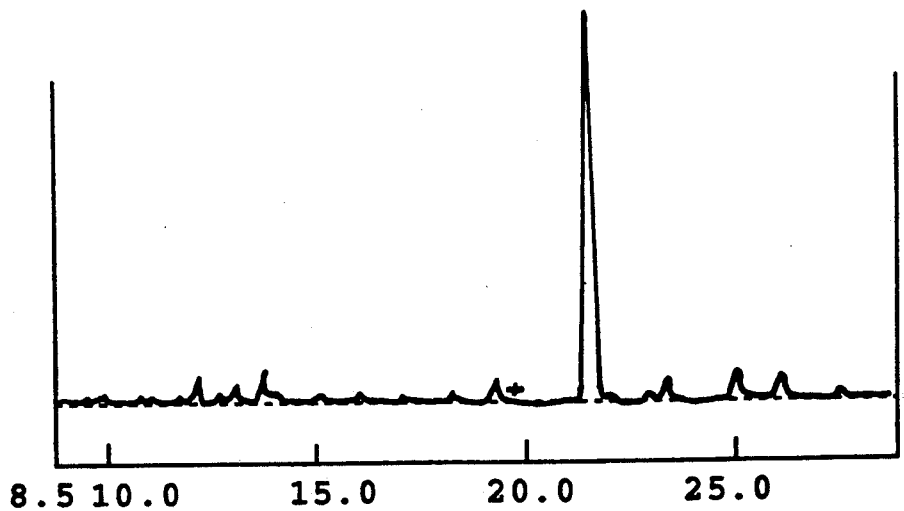
Figure 9A:
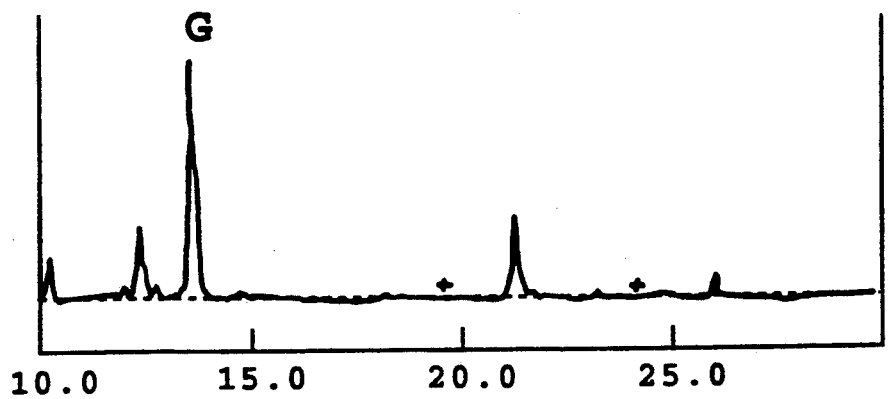
FIGS. 9A–9J show HPLC chromatograms of the first-tenth cycles, respectively, in the C-terminal sequencing of 2.5 nmoles A15G polypeptide.
Figure 9B:
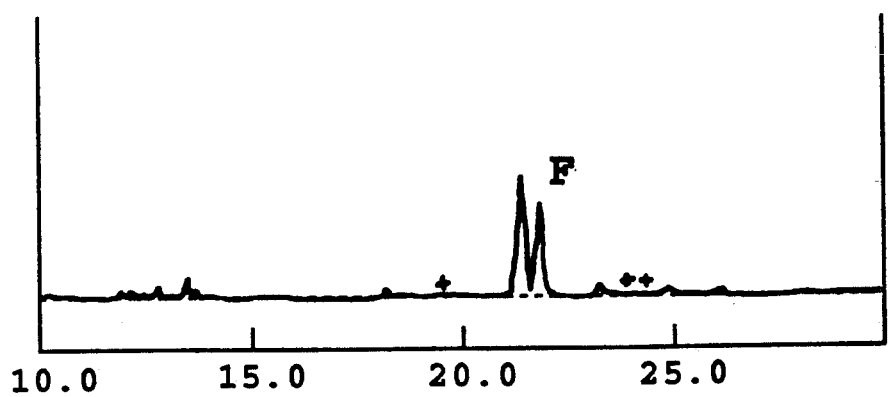
Figure 9C:
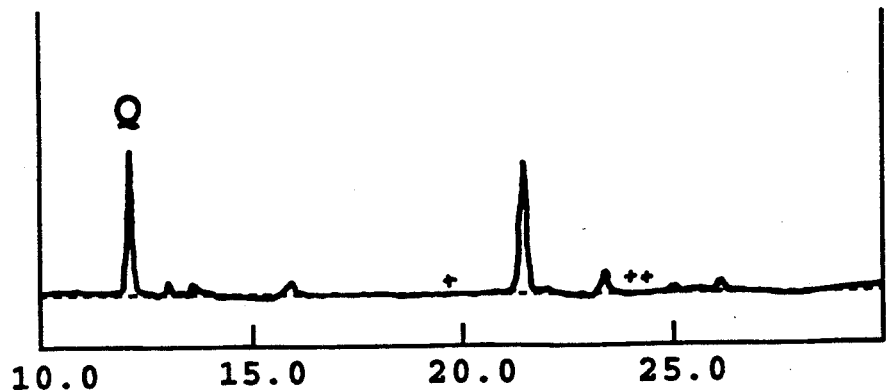
Figure 9D:
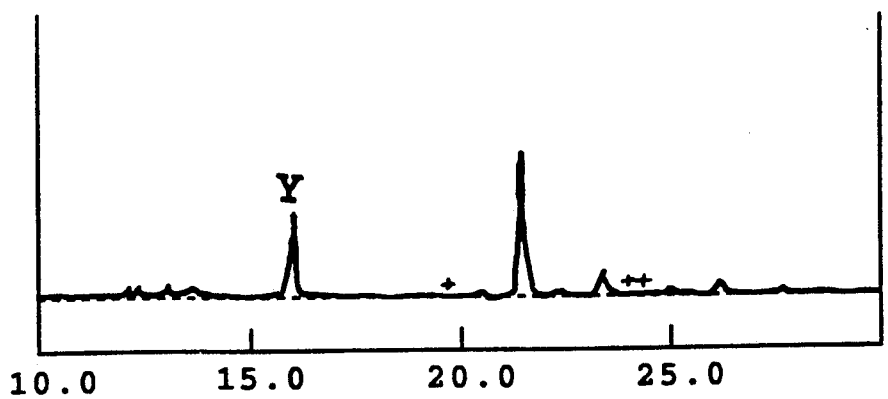
Figure 9E:
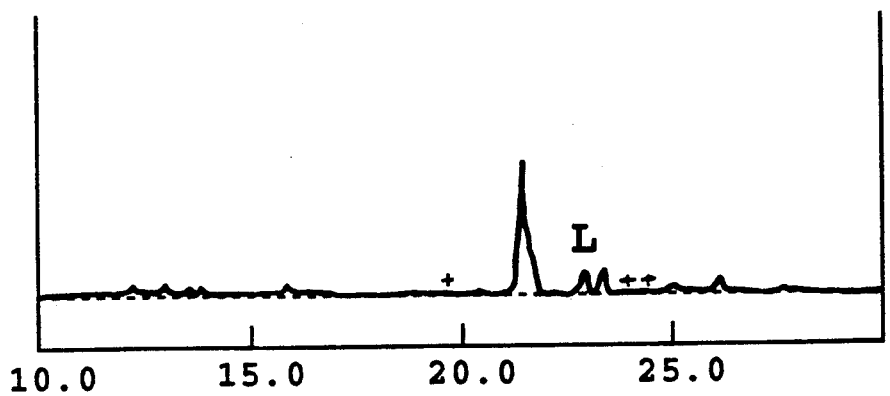
Figure 9F:
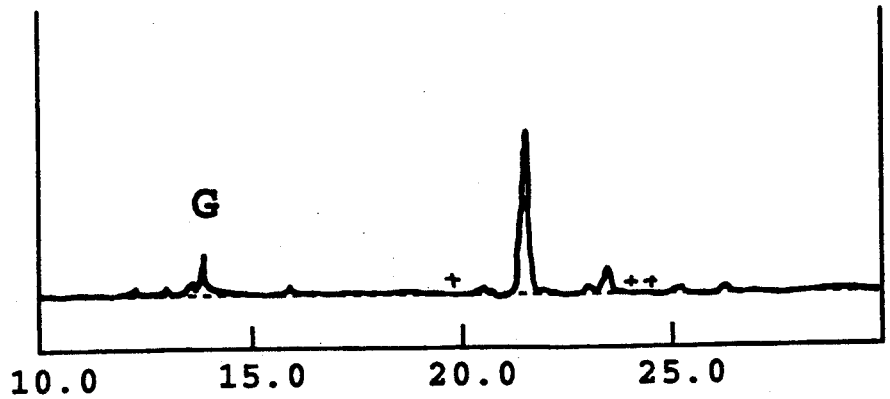
Figure 9G:
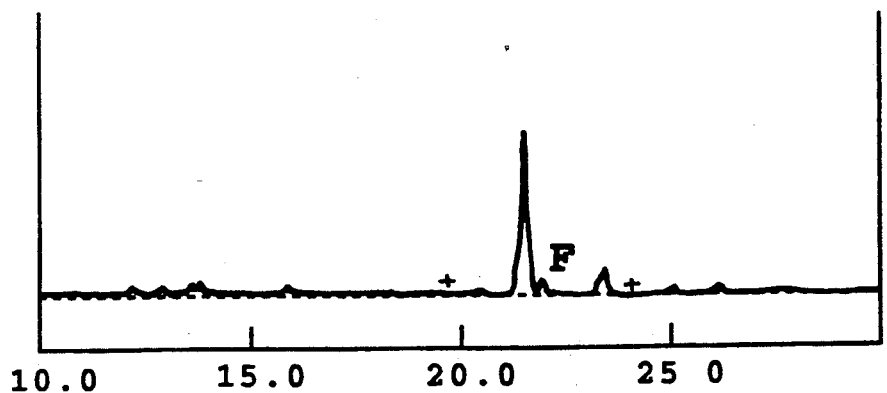
Figure 9H:
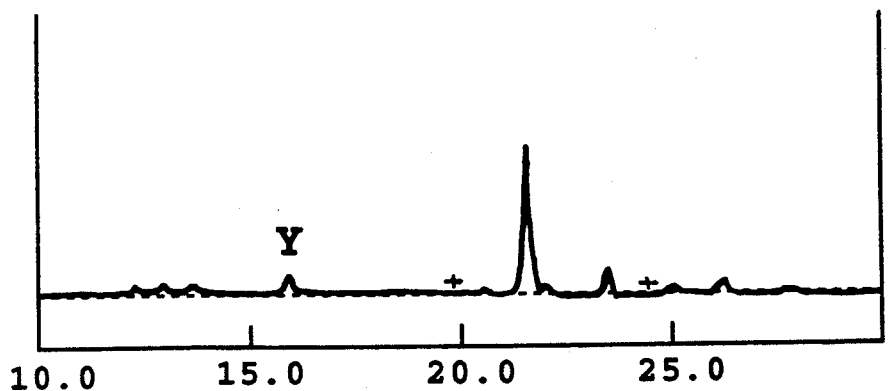
Figure 9I:
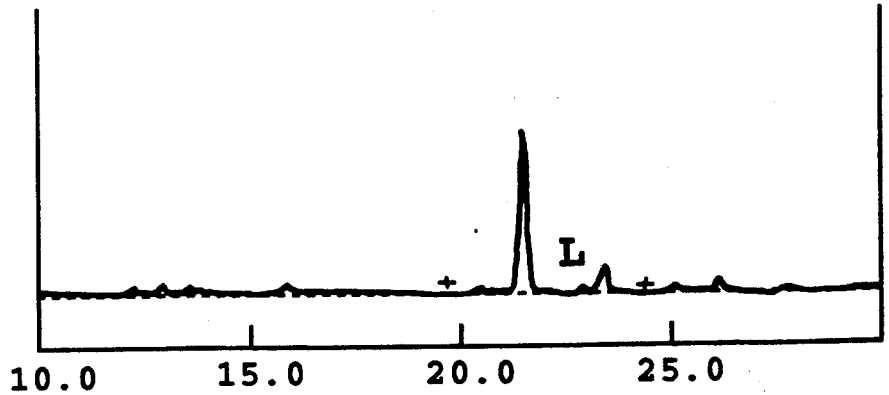
Figure 9J:
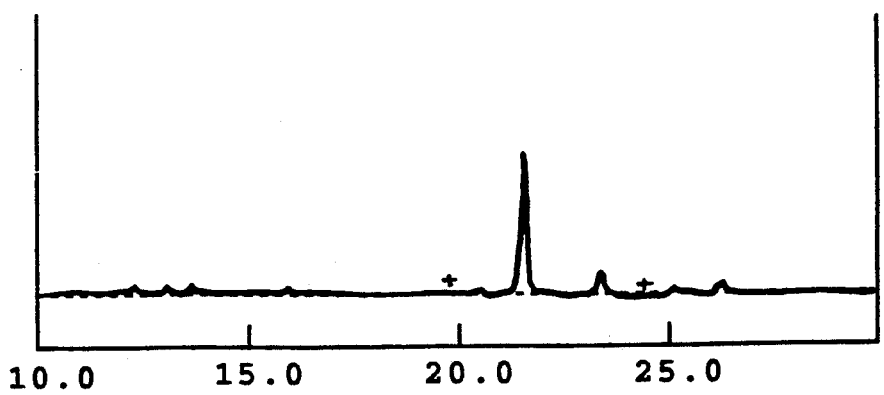

FIG. 7A shows the HPLC profile of the first round of C-terminal sequencing. The sample applied to the column included the released modified amino acid TH. The amino acid TH peak was verified by its migration on HPLC against a known standard, modified amino acid TH. The other peaks in the HPLC profile are background peaks observed from cycle to cycle.

C. Repeated Sequencing Cycles

The reaction sequence described above was repeated through four rounds of sequencing, with the results shown in FIGS. 7B-7E. The second amino acid thiohydantoin is readily identified as Gln; the third, as Phe; the fourth, as Gly; and the fifth, as Leu.

EXAMPLE 12

Automated C-Terminal Sequencing of β-Lactoglobulin

This example demonstrates the use of the method to determine the C-terminal amino acid sequence of five terminal amino acids of β-lactoglobulin. In this method 2.65 mgs of β-lactoglobulin on polystyrene (about 1.5 nmole) was sequenced coupled to polystyrene, as above. The amino acid sequence of the five C-terminal peptides is:

R-GluGlnCysHisIle

After coupling the peptide to polystyrene resin, via the N-terminus and the epsilon-amine groups of lysine, the C-terminal carboxyl group was reacted in a manner similar to that of Example 4, to form the thiohydantoin. The polypeptide on the solid support was subjected to five rounds of C-terminal sequencing, using the automated sequencer steps given in Example 11. The HPLC profiles of the five rounds of TH formation and cleavage are shown in FIGS. 8A-8E, respectively. The first amino acid thiohydantoin is readily identified as Ile; the second, as His; the third, as Cys; and fourth, as Gln, and the fifth, as Glu.

EXAMPLE 13

Automated C-Terminal Sequencing of A15G Peptide

This example demonstrates the use of the method to determine the C-terminal amino acid sequence of ten terminal amino acids of the peptide A15G. In the method 1.1 mg of the peptide on polystyrene (about 2.5 nmole) was sequenced as above. The amino acid sequence of the peptide is:

Fmoc-AlaLysGlyLysLeuTyrPheGlyLeuTyrGln-PheGly

After coupling the peptide to polystyrene resin, the C-terminal carboxyl group was reacted in a manner similar to that of Example 4, to form the thiohydantoin. The polypeptide on the solid support was subjected to ten rounds of C-terminal sequencing, using the automated sequencer steps given in Example 11. The HPLC profiles of the ten rounds of TH formation and cleavage are shown in FIGS. 9A–9J, respectively.

Clearly detectable amino acid thiohydantoin signals were obtained out to the ninth round of cycling.

Although the invention has been described with reference to particular reagents, and methods, it will be evident that the various other embodiments, uses, and reagents may be employed without departing from the invention.

What is claimed is:

1. A method for cleaving the acyl-thiohydantoin bond in an acyl thiohydantoin, comprising:
   (a) contacting the acyl thiohydantoin with an alkylating agent under conditions effective to form an adduct on the thiohydantoin by alkylation; and
   (b) reacting the adduct-containing acyl-thiohydantoin from (a) above with a cleaving agent under substantially anhydrous, acidic conditions to cause cleavage of the acylthiohydantoin bond, with release of an adduct-containing thiohydantoin.

2. The method of claim 1, wherein said contacting is carried out at an effective pH of greater than 7.

3. The method of claim 1, wherein said acyl thiohydantoin is a peptidyl thiohydantoin formed at the C-terminal amino acid of a peptide, and said acyl thiohydantoin and the released adduct-containing thiohydatoin include the side chain of said C-terminal amino acid.

4. The method of claim 1, for use in C-terminal amino acid sequencing of a polypeptide, wherein said cleaving agent is an isothiocyanate, and said cleaving is effective to produce an acyl thiohydantoin with the penultimate C-terminal amino acid.

5. The method of claim 4, wherein said cleaving agent includes trimethylsilyl isothiocyanate.

6. The method of claim 4, which further includes identifying the amino acid from which the released thiohydantoin was formed.

7. The method of claim 6, wherein the alkylating agent contains a detectable label.

8. A method for C-terminal amino acid sequencing of a polypeptide which method comprises the steps:
   (a) converting the C-terminal amino acid of the polypeptide to an acyl-thiohydantoin which is joined to the penultimate C-terminal amino acid through an acyl-thiohydantoin bond;
   (b) contacting the C-terminal peptidyl acyl-thiohydantoin of (a) with an alkylating agent under conditions effective to form an adduct on the thiohydantoin by alkylation;
   (c) reacting the adduct-containing acyl-thiohydantoin from (b) above with a cleaving agent under substantially anhydrous, acidic conditions to cause cleavage of the acylthiohydantoin bond, with release of an adduct-containing thiohydantoin from the remaining, shortened polypeptide;
   (d) converting the C-terminal of the shortened polypeptide to an acyl-thiohydantoin which is joined to the penultimate C-terminal amino acid of the shortened polypeptide through an acyl-thiohydantoin bond;
   (e) separating the released thiohydantoin from the remaining, shortened polypeptide and identifying the amino acid residue in the released product; and
   (f) repeating steps (b)–(e) with each successively shortened polypeptide.

9. The method of claim 8, wherein steps (c) and (d) are combined by employing, as the cleaving agent, a substantially anhydrous acidic isothiocyanate or a mixture of trifluoroacetic acid and a silylisothiocyanate.

10. The method of claim 9, wherein said cleaving agent includes trimethylsilyl isothiocyanate.

11. The method of claim 8, wherein the alkylating agent contains a detectable label, and said identifying includes comparing the migration characteristics of the released, labeled product on HPLC with a known standard.

* * * * *

UNITED STATES PATENT AND TRADEMARK OFFICE
CERTIFICATE OF CORRECTION

PATENT NO. : 5,185,266
DATED : 02/09/93
INVENTOR(S) : VICTORIA LEE BOYD; GERALD ZON

It is certified that error appears in the above-identified patent and that said Letters Patent is hereby corrected as shown below:

In Column 15, line 19, change "Peotidtl-TH" to --Peptidyl-TH-- .

Signed and Sealed this

Eighteenth Day of January, 1994

Attest:

BRUCE LEHMAN

Attesting Officer

Commissioner of Patents and Trademarks